United States Patent [19]

Herrin et al.

[11] 4,150,125

[45] Apr. 17, 1979

[54] TRIGLYCERIDE ESTER OF PHOSPHONOACETIC ACID HAVING ANTIVIRAL ACTIVITY

[75] Inventors: Thomas R. Herrin, Waukegan; John S. Fairgrieve, Lake Villa, both of Ill.

[73] Assignee: Abbott Laboratories, North Chicago, Ill.

[21] Appl. No.: 907,368

[22] Filed: May 19, 1978

Related U.S. Application Data

[60] Continuation-in-part of Ser. No. 838,430, Sep. 30, 1977, abandoned, which is a division of Ser. No. 681,574, Apr. 30, 1976, Pat. No. 4,052,439.

[51] Int. Cl.$^2$ ............... A01N 9/36; A61K 31/66; C07C 67/00; C07C 69/02
[52] U.S. Cl. ................................ 424/212; 260/403; 560/129; 560/263
[58] Field of Search ............... 260/403; 560/129, 263; 424/212

[56] References Cited

U.S. PATENT DOCUMENTS

| | | | |
|---|---|---|---|
| 3,767,795 | 10/1973 | Schleicher | 424/212 |
| 3,988,446 | 10/1976 | Paris | 260/403 X |
| 4,016,264 | 5/1977 | Clark | 424/212 |

*Primary Examiner*—John Niebling
*Attorney, Agent, or Firm*—Paul D. Burgauer; Robert L. Niblack

[57] ABSTRACT

A triglyceride carrying, in the $\beta$-position, the anionic moiety of phosphonoacetic acid has been found to exhibit excellent activity against viral infections caused by a herpes virus.

11 Claims, No Drawings

TRIGLYCERIDE ESTER OF PHOSPHONOACETIC ACID HAVING ANTIVIRAL ACTIVITY

HISTORY OF THIS APPLICATION

This application is a continuation-in-part of U.S. application Ser. No. 838,430, filed Sept. 30, 1977, now abandoned, which, in turn, was a Divisional application of Ser. No. 681,574, filed Apr. 30, 1976, now U.S. Pat. No. 4,052,439.

DETAILED DESCRIPTION OF THE INVENTION

Phosphonacetic acid has been known for many years, although its use as an antiviral agent has only been discovered in recent years. U.S. Pat. No. 3,767,795 clearly demonstrates the high activity of phosphonacetic acid as a topical, intraperitoneal or oral agent effective in combating infections by herpes dermatitis, herpes genitalis, herpes keratitis, herpes encephalitis and vaccinia virus. However, oral products containing phosphonoacetic acid have not been tolerated by all animals in need of such treatment in that the nature of the active ingredient sometimes causes disturbances in the gastrointestinal tract such as heartburn, gastric lesions, and the like.

The present invention is, therefore, directed to an antiviral compound that does not exhibit the above-named side affects, but otherwise exhibits the same beneficial results. The compounds are represented by the formula

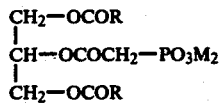

wherein M is hydrogen or a pharmaceutically acceptable cation and R is an alkyl group of 1–17 carbon atoms which may optionally contain one or more carbon-to-carbon unsaturation. The triglycerides of Structure I thus carry in the α- and γ- positions an acyl moiety derived from a saturated or unsaturated aliphatic or olefinic acid and can be depicted as

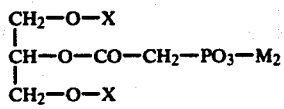

wherein X represents the acyl group of a saturated or unsaturated alkyl carboxylic acid. The saturated or unsaturated alkyl group just mentioned preferably contains an uneven number of carbon atoms, as acids of that configuration are more common and, thus, commercially easier available. The length of the alkyl group is almost of no significance except that it affects the molecular weight of the compound of Structure I. The above R, therefore, is usually represented by methyl, propyl, pentyl, hexyl, nonyl, undecanyl, pentadecyl or heptadecyl, or X is the acyl moiety of the unsaturated series represented by acryloyl, crotonoyl, linoloyl, oleoyl or the corresponding polyunsaturated acyl moieties and the like. Preferred M cations are hydrogen, sodium, ammonium or potassium.

In a general embodiment of the present invention, the compounds of Structure I are made by esterifying dihydroxy acetone with the desired acid of the formula RCOOH, their anhydride or the corresponding acyl halide. The oxo group of the obtained 1,3-diacylacetone is then reduced to produce the corresponding diglyceride ester. This reduction can be done catalytically when the R groups do not contain any unsaturated links that are to be maintained or, chemical means can be used to reduce the oxo group to a hydroxy group. In turn, the diacyl glyceride is then treated with chloroacetic acid chloride which forms the 1,3-diacyl-2-chloroacetyl ester of glycerol. This is then treated with tris(trimethylsilyl) phosphite to produce 1,3-diacyl-2-[P,P-bis(trimethylsilyl)phosphonoacetyl]glycerol. Careful hydrolysis of the latter with aqueous sodium bicarbonate yields the desired triester of structure I.

The new glycerol triester is not only less irritating to the gastrointestinal tract of animals to which said compound is administered, but it also has higher lipid solubility than the parent compound phosphonoacetic acid, and, therefore, is much better suited for topical application, penetrating the epidermis of the animal from an ointment base more rapidly than the parent compound.

In order to illustrate the preparation and use of the new compound, reference is made to the following examples which, however, are not intended to limit the invention in any respect.

EXAMPLE I

A solution of 8.8 g of 1,3-diacetylglycerol, and 4.4 g of pyridine in 100 ml of benzene is cooled in an icebath. A solution of 6.16 g of chloroacetyl chloride in 20 ml of benzene is dropwise added and the mixture is allowed to warm gradually to room temperature. It is filtered and the solvent is evaporated. The residual liquid is distilled: the first fraction boiling up to 90° C./40μ is discarded; the second fraction (105° C./40μ) represents 10.98 g of crude 1,3-diacetyl-2-chloroacetyl glycerol. The material is chromatographed on 250 g of 100–200 mesh Florisol ®, using 15% acetone in petroleum ether (boiling point 60°–80° C.) as eluant. The first six fractions are combined and distilled at 100° C./20μ to give 7.38 g of the purified triglyceride.

This material is combined with 18 g of tris(trimethylsilyl)phosphite and heated in a 165° C. oil bath for 1 hour and the material is then distilled. The yellow-green residue is distilled, and the fraction boiling at 150° C./30μ is collected and identified as 12.11 g of 1,3-diacetyl-2-[P,P-bis(trimethylsilyl)phosphonoacetyl]-glycerol.

To 4.77 g of this material is added a solution of 1.865 g of sodium bicarbonate in 20 ml of water. The solution is then evaporated whereby some material is lost due to frothing. The residue is dried by azeotropic distillation with ethanol and then placing the residue in a 1 mm vacuum overnight at 40° C., producing 3.27 g of an amorphous flaky solid, analyzing properly as the disodium salt of 1,3-diacetyl-2-phosphonoacetyl-glycerol of molecular weight 342.153.

EXAMPLE II

Using the procedure of the above example, but starting with an equimolar amount of 1,3-dipalmitoyl glycerol, 1,3-dipalmitoyl-2-[P,P-bis(trimethylsilylphosphonoacetyl)] glycerol is obtained. After the solvents are evaporated, the residue is dissolved in the necessary minimal amount of tetrahydrofuran and water is added to promote hydrolysis which takes place within a few minutes at room temperature to produce the free acid, 1,3-dipalmitoyl-2-phosphonoacetyl glycerol. The material is purified by azeotropic distillation with benzene and crystallizing it from ether to produce the pure material melting at 84°-5° C.

EXAMPLE III

Animal cells, after infection by herpes simplex virus, produce a new DNA polymerase which has different physical-chemical properties to DNA polymerases in normal animal cells. The replication of herpes virus depends on the virus-induced DNA polymerase. Inhibition of this virus-induced enzyme will stop the replication of herpes virus. An aqueous solution of the disodium salt of the triglyceride of Example I and II produce 68% and 73%, respectively, of such inhibition at a concentration of 166 μg/ml.

EXAMPLE IV

The effectiveness of the triglyceride of Example I (disodium salt) is determined in the following manner: female CF mice weighing about 20 g, are denuded on a 20 mm$^2$ area of their backs under light ether anesthesia. Herpes virus ($10^7 TCID_{50/ml}$) is applied to the denuded skin and impregnated into the dermis with a 27-gauge sterile hypodermic needle. Herpes lesions or vesicles usually develop in 3-5 days. The test is allowed to continue for a total of 10 days. The mice that are treated topically have the drug applied to the site of the infection as a 2% aqueous solution 2 hours after the virus is introduced into the skin and twice daily thereafter for five consecutive days. The drug is thus applied a total of 11 times. A single application of a 2% drug solution delivers approximately 2 mg of the active material.

The mice that are treated orally have drug delivered by gavage 2 hours after infection and twice daily for five consecutive days thereafter. The Mann-Whitney "U" test (Siegal; Non-Parametric Statistics for the Behavioral Science, McGraw-Hill, New York 1956, page 116) is used to statistically analyze the herpes infection in mice by making paired comparisons between the virus treated and untreated control groups. Those groups that show statistically significant differences from the virus-controlled group are defined as "active". The results of this test are shown in the following table using the disodium salts of the triglyceride of Example I as "Test Compound."

TABLE I

| Treatment | No. of Mice | Route | No. of Mice Dead | No. of Mice Paralyzed | Significant Level |
|---|---|---|---|---|---|
| Normal Control | 10 | — | 0 | 0 | — |
| Virus Control | 10 | — | 9 | 1 | — |
| Test Compound | 10 | 2%-Topical | 0 | 3 | P<.05 |
| Test Compound | 10 | Oral 0.8g/kg day | 0 | 1 | P<.05 |

By using the free acid of the compound shown in Example II, essentially the same results are obtained as shown in the above table.

Similar results as shown in Example IV are obtained when using herpes keratitis, herpes encephalitis, herpes genitalis or herpes dermatitis cultures as the infectant. Also, the compounds of Structure II wherein each R group represents the acyl group of hexanoic, octanoic, linoleic, crotonic or oleic acids produce results very closely analogous to those shown in Examples III and IV. In all instances, it appears to be immaterial whether the free acid, the monosodium, disodium, potassium or even ammonium salts are used in determining the inhibition level shown in Example III.

In determining the required dosage for a daily treatment regimen, the above reference U.S. Pat. No. 3,767,795 can be used for guidance. Of course, the amount of I must be increased over the dose shown in the reference due to and depending on the molecular weight of the specific R selected. It is assumed that when the new triglyceride enters the blood stream it will be cleaved into free phosphonoacetic acid and for that reason, the dose should be adjusted on the basis of the phosphonoacetic moiety in I while otherwise being selected to levels shown in the reference.

The compounds for Structure I can easily be compounded into a dosage unit form for medicinal use. For instance, pharmaceutical tablets can be prepared by mixing the active material with the usual type of adjuvants, flavoring agents, fillers, buffers and/or coloring agents which together with a lubricant can be compressed into the usual tablets. Also, a mixture of the above active compound with fillers and/or buffers or solid diluents can be processed into wafers, pills or just simply filled into gelatin capsules in dosages of suitable amounts. Preferably, a dosage unit contains between 250-1250 mg of the active ingredients, and tablets of this type are preferrably prepared in disected form.

The oral dosage forms of the type indicated above do not require any coating for the purpose of taste masking or protection against the acid environment of the stomach. The active ingredient I alone does not cause any gastrointestinal discomforts as it is absorbed as a glyceride. The new drug is lipid soluble and as such penetrates the cell membranes and will be found in the blood stream at sufficiently high doses to provide the antiviral effect. The same effect can be obtained, as shown above, by topically applying a salve, ointment, emulsion, suspension or solution of the glyceride topically to the affected skin area.

The following is a typical formulation which may be used to incorporate the compound of the present invention into a tablet form. About one half of 52 g of cornstarch is milled together with 500 g of the active drug and 220 g of calcium phosphate dibasic dihydrate; this blend is milled and passed through a 40-mesh screen. The remaining portion of the cornstarch is granulated with water, heated and mixed with the above blend in a hot air over at 50° C. and sifted through a 16-mesh screen. These granules are then mixed with 16 g of talcum powder and 4 g of magnesium stearate, the mixture is blended and subsequently passed through a 30-mesh screen and blended for at least 15 minutes. In order to prepare tablets, this mixture is compressed using a 9/32" standard convex punch producing a tablet of hardness 7-9 with each tablet weighing 800 mg and containing 500 mg of the active drug.

A simple topical administration vehicle is made as follows: 2-15 parts of the above tri-ester is stirred into warm petrolatum in an amount to prepare 100 parts by weight of an ointment. When desired, the mixture may be milled to achieve a desirable particle size and, if desired, a sufficient amount of a pharmaceutically acceptable wax is added to achieve the chosen consistency of the ointment.

What is claimed is:

1. A triglyceride of the formula

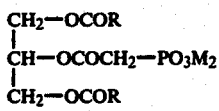

wherein R is an alkyl group of 1-17 carbon atoms which may optionally contain one or more carbon-to-carbon unsaturation, and wherein M is hydrogen or a pharmaceutically acceptable cation.

2. The compound of claim 1 wherein R is methyl and M is hydrogen.

3. The compound of claim 1 wherein R is methyl and M is sodium.

4. The compound of claim 1 wherein R is pentadecyl and M is hydrogen.

5. A pharmaceutical preparation for topical application as an anti-viral composition containing as the active ingredient a compound of the formula

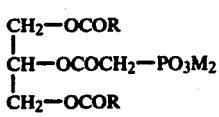

wherein R is an alkyl group of 1-17 carbon atoms which may optionally contain one or more carbon-to-carbon unsaturation, and wherein M is hydrogen or a pharmaceutically acceptable cation, homogeneously distributed in a carrier suitable for topical application to areas of an animal body afflicted by a herpes infection.

6. The compound of claim 5 wherein R is methyl and M is hydrogen.

7. The compound of claim 5 wherein R is methyl and M is sodium.

8. The compound of claim 5 wherein R is pentadecyl and M is hydrogen.

9. A pharmaceutical composition which when administered orally is effective against a herpes virus infection and whose active ingredient in this composition is a compound of the formula

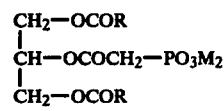

wherein R is an alkyl group of 1-17 carbon atoms which may optionally contain one or more carbon-to-carbon unsaturation, and wherein M is hydrogen or a pharmaceutically acceptable cation.

10. The composition of claim 9 in dosage unit form.

11. The composition of claim 10 wherein R is methyl and M is sodium.

* * * * *